US012605108B2

(12) United States Patent
Minati et al.

(10) Patent No.: US 12,605,108 B2
(45) Date of Patent: Apr. 21, 2026

(54) DEVICE FOR CONDUCTING A MULTIPARAMETRIC EXAMINATION OF THE SKIN OF A PERSON AND A SYSTEM INCLUDING SAID DEVICE

(71) Applicant: ALMA MAGISTRA S.R.L.S., Genoa (IT)

(72) Inventors: Ludovico Minati, Grigno (IT); Davide Antichi, Campomorone (IT); Marco Muraccini, Santarcangelo di Romagna (IT); Renato Colognato, Ispra (IT)

(73) Assignee: ALMA MAGISTRA S.R.L.S., Genoa (IT)

( * ) Notice: Subject to any disclaimer, the term of this patent is extended or adjusted under 35 U.S.C. 154(b) by 318 days.

(21) Appl. No.: 18/546,392

(22) PCT Filed: Mar. 11, 2022

(86) PCT No.: PCT/IT2022/050050
§ 371 (c)(1),
(2) Date: Aug. 14, 2023

(87) PCT Pub. No.: WO2022/195637
PCT Pub. Date: Sep. 22, 2022

(65) Prior Publication Data
US 2024/0090824 A1 Mar. 21, 2024

(30) Foreign Application Priority Data

Mar. 18, 2021 (IT) ........................ 102021000006524

(51) Int. Cl.
*A61B 5/00* (2006.01)
*A61B 5/01* (2006.01)
(Continued)

(52) U.S. Cl.
CPC ............ *A61B 5/441* (2013.01); *A61B 5/0013* (2013.01); *A61B 5/0064* (2013.01); *A61B 5/01* (2013.01);
(Continued)

(58) Field of Classification Search
None
See application file for complete search history.

(56) References Cited

U.S. PATENT DOCUMENTS 10,105,101 B2 * 10/2018 Fougere ................. A61B 5/684
10,542,918 B2 * 1/2020 Conrad .................. A61B 5/681
(Continued)

FOREIGN PATENT DOCUMENTS

EP 2290583 A1 3/2011
KR 101274303 B1 6/2013
(Continued)

OTHER PUBLICATIONS

Clarivate Analytics, translation of KR-101318607-B1 (Year: 2025).*
(Continued)

*Primary Examiner* — Carl H Layno
*Assistant Examiner* — Manolis Pahakis
(74) *Attorney, Agent, or Firm* — NIXON & VANDERHYE

(57) ABSTRACT

Disclosed is a device including a skin microscope for acquiring images at different wavelengths of one or more areas of a person's skin. The device includes one or more pH sensors, one or more temperature sensors, a bioimpedance sensor and a pulse oximeter included in the device so that, together with the acquisition of a skin image, it is possible to co-register the temperature, the bioimpedance and saturation of hemoglobin in the field of view of the microscope, and the pH in the immediate vicinity of that field of view. The device can be connected to an electronic device, such as
(Continued)

a "smartphone", for the transmission of the acquired data to the latter, possibly after they have undergone initial processing using specific algorithms.

20 Claims, 3 Drawing Sheets

(51) Int. Cl.

| | | |
|---|---|---|
| A61B 5/0531 | (2021.01) | |
| A61B 5/145 | (2006.01) | |
| A61B 5/1455 | (2006.01) | |

(52) U.S. Cl.

CPC ........ *A61B 5/0531* (2013.01); *A61B 5/14539* (2013.01); *A61B 5/14551* (2013.01); *A61B 2560/0443* (2013.01); *A61B 2560/0462* (2013.01); *A61B 2562/0233* (2013.01); *A61B 2562/0271* (2013.01)

(56) References Cited

U.S. PATENT DOCUMENTS

| | | | | |
|---|---|---|---|---|
| 10,925,534 | B2 * | 2/2021 | Chung | A61B 5/743 |
| 11,439,327 | B2 * | 9/2022 | Park | G01J 3/027 |
| 2003/0216663 | A1 * | 11/2003 | Jersey-Willuhn | A61B 5/412 |
| | | | | 977/932 |
| 2006/0106375 | A1 * | 5/2006 | Werneth | A61B 18/1492 |
| | | | | 606/41 |
| 2008/0296514 | A1 * | 12/2008 | Metzger | G01N 21/1717 |
| | | | | 600/407 |
| 2010/0185064 | A1 * | 7/2010 | Bandic | A61B 5/444 |
| | | | | 600/306 |
| 2012/0041284 | A1 | 2/2012 | Krishnan et al. | |
| 2015/0230863 | A1 * | 8/2015 | Youngquist | A61B 18/203 |
| | | | | 606/9 |

| | | | | |
|---|---|---|---|---|
| 2015/0289929 | A1 * | 10/2015 | Toth | A61N 1/303 |
| | | | | 606/41 |
| 2016/0133010 | A1 * | 5/2016 | Hamada | G06T 7/11 |
| | | | | 382/128 |
| 2016/0133011 | A1 * | 5/2016 | Nakajima | G06T 7/0012 |
| | | | | 382/128 |
| 2016/0189377 | A1 * | 6/2016 | Houjou | G06T 7/0012 |
| | | | | 382/133 |
| 2016/0191882 | A1 * | 6/2016 | Nakajima | G06T 5/92 |
| | | | | 382/167 |
| 2016/0275675 | A1 * | 9/2016 | Nakajima | G06T 5/70 |
| 2016/0331308 | A1 * | 11/2016 | Zhou | A61M 35/003 |
| 2017/0164878 | A1 * | 6/2017 | Connor | G09B 19/00 |
| 2019/0015023 | A1 * | 1/2019 | Monfre | A61B 5/7278 |
| 2020/0037882 | A1 * | 2/2020 | Westerhof | A61B 5/6898 |
| 2020/0268252 | A1 * | 8/2020 | Litvinova | G01J 3/4406 |
| 2020/0390362 | A1 * | 12/2020 | Westerhof | A61B 5/442 |
| 2021/0113121 | A1 * | 4/2021 | Diab | A61B 5/0073 |
| 2021/0145251 | A1 * | 5/2021 | Rusoke-Dierich | |
| | | | | A61B 1/00105 |
| 2021/0161390 | A1 * | 6/2021 | Kasprzak | A61B 5/448 |
| 2023/0296447 | A1 * | 9/2023 | Maruyama | A61B 5/01 |
| | | | | 338/22 R |

FOREIGN PATENT DOCUMENTS

| | | | | | |
|---|---|---|---|---|---|
| KR | | 101318607 | B1 * | 10/2013 | A61B 5/0002 |
| WO | WO-2014098363 | A1 * | 6/2014 | A61B 5/0531 |

OTHER PUBLICATIONS

Clarivate Analytics, translation of WO-2014098363-A1 (Year: 2025).*
International Search Report for PCT/IT2022/050050 mailed Jul. 8, 2022, 4 pages.
Written Opinion of the ISA for PCT/IT2022/050050 mailed Jul. 8, 2022, 9 pages.

\* cited by examiner

DEVICE FOR CONDUCTING A MULTIPARAMETRIC EXAMINATION OF THE SKIN OF A PERSON AND A SYSTEM INCLUDING SAID DEVICE

CROSS-REFERENCE TO RELATED APPLICATIONS

This application is the US national stage of PCT/IT2022/050050, filed Mar. 11, 2022 and designating the United States, which claims the priority of IT 102021000006524, filed Mar. 18, 2021. The entire contents of each foregoing application are incorporated herein by reference.

BACKGROUND OF THE INVENTION

Field of the Invention

The present invention finds application in the fields of dermatological clinic, cosmetics and aesthetic medicine. The present invention concerns, in particular, the initial phase of the diagnostic process, i.e., the phase in which the skin of a patient is examined in order to allow a doctor or a cosmetologist to express a judgment of a clinical nature (such as the recognition of a pathological condition or the cause of a blemish).

More precisely, the present invention refers to a device using which a person can autonomously acquire information about the state of his own skin, and possibly send said information to a doctor (such as for example, a dermatologist) or a cosmetologist in order to allow the latter to formulate a diagnosis. The present invention also relates to a system for conducting a multiparametric examination of the skin of a person, including the aforementioned device.

Description of the Related Art

In order to facilitate a doctor or a cosmetologist in conducting a diagnostic examination of the skin of a person, devices have been devised that include a skin microscope at low magnification illuminated with incident light and integrating one or more sensors for carrying out appropriate measurements to be combined with the images acquired by the microscope. Such devices are described, by way of example, in WO 2014 098363 A1 and in US 2012 041284 A1.

In the known devices mentioned above, however, although the sensors can perform measurements simultaneously with the acquisition of images by the skin microscope, the detection of some of the aforementioned sensors take place in areas of the skin not strictly related to those displayed by the microscope (that is not sufficiently correlated to the visual field of the skin microscope to be able to qualify the aforesaid sensors as actually adjuvants of said microscope).

SUMMARY OF THE INVENTION

The purpose of the present invention is to overcome the aforementioned drawbacks by indicating a device for conducting a multiparametric examination of the skin of a person in which the images acquired by a skin microscope included in the device can be combined with measurements made by sensors (also included in the device) directly in the area of the skin viewed by the microscope or in the immediate vicinity of the latter, preferably in such a way as to be able to deduce what the aforementioned detection would have been if it had been carried out in the visual field of the microscope The subject of the present invention is a device for conducting a multiparametric examination of the skin of a person, said device comprising:

a support structure in correspondence with which said device:

it is graspable by a person and when grasped by a person, it can be brought into contact with the skin of said person in correspondence with an area of said skin for carrying out a multiparametric examination in said area;

a skin microscope included in said device in such a way that, when said device is in contact with the skin of a person in correspondence with said area of skin, said microscope is suitable for acquiring an image of at least a first portion of said area of skin (with said first portion of said skin zone corresponding to the visual field of the microscope);

at least one illuminator suitable for emitting electromagnetic radiations and included in said device in such a way that, when said device is in contact with the skin of a person in correspondence with said area of skin, the electromagnetic radiation emitted by said illuminator:

impacts against said skin area at least in correspondence with said first portion of said skin area (of which said microscope is suitable for acquiring an image), i.e., at least in correspondence with the visual field of the microscope and, after having been at least partially reflected and/or dispersed from said first portion of said skin zone, at least partially affect the optics of said microscope;

first measuring means suitable for measuring the pH and included in said device in such a way that, when said device is in contact with the skin of a person in correspondence with said area of skin, said first measuring means are suitable for measuring the pH of the skin of said person at least in correspondence with a second portion of said skin area adjacent to said first portion of said skin area (of which said microscope is suitable for acquiring an image), i.e., adjacent to the visual field of the microscope, wherein, according to the invention, said device comprises:

a plurality of said illuminators, each of which is suitable for emitting electromagnetic radiation in at least a range of wavelengths, each of said illuminators being suitable for emitting electromagnetic radiations having a wavelength not less than 100 nm and not greater than 1 mm (i.e., suitable for emitting infrared radiation and/or ultraviolet radiation and/or radiation belonging to the visible spectrum);

second measuring means suitable for measuring the temperature and included in said device in such a way that, when said device is in contact with the skin of a person in correspondence with said area of skin, said second measuring means are suitable for measuring skin temperature of that person:

at least in correspondence with said first portion of said skin area (of which said microscope is suitable for acquiring an image), i.e., at least in correspondence with the visual field of the microscope and/or at least in correspondence with a third portion of said skin area adjacent to said first portion of said skin area (of which said microscope is suitable for acquiring an image), i.e., adjacent to the visual field of the microscope).

Incidentally and for the avoidance of doubt, said second portion of said skin area could coincide with or be superimposed onto said third portion of said skin area;

third measuring means suitable for measuring the impedance of body tissues of a person, said third measuring means comprising at least one pair of electrodes included in said device in such a way that, when said device is in contact with the skin of a person in correspondence with said area of skin, said electrodes are in contact with the skin of said person respectively on opposite sides with respect to said first portion of said skin area (of which said microscope is suitable for acquiring an image), so that the visual field of the microscope is interposed between said electrodes, said third measuring means being suitable for applying a potential difference between said pair of electrodes, when said device is in contact with the skin of a person in correspondence with said skin zone, said third measuring means being suitable for calculating the impedance of body tissues included in said zone, at least in correspondence with said first portion of said zone of skin (of which said microscope is suitable for acquiring an image), i.e., at least in correspondence with the visual field of the microscope, by measuring an alternating electric current passing through said body tissues following the application to them of a potential difference through said electrodes.

The third measuring means preferably comprise a bioimpedance sensor which, by means of a pair of electrodes, applies a small potential difference in alternating electric current to the skin. This allows to measure the bioimpedance of the skin as a function of the applied frequency. The foregoing is extremely advantageous since the skin comprises body tissues characterized by different bioimpedances. By measuring the bioimpedance of the skin at different frequencies, it is therefore possible to estimate the tissue composition in the field of view of the microscope.

The fact that the field of view of the microscope is interposed between the electrodes is an advantage not only because it allows to measure the bioimpedance in the field of view of the microscope, but also because the skin depth at which the alternating electric current passes through the body tissues grows as it grows the distance between the electrodes. In this case, by placing the electrodes on opposite sides of the microscope field of view, the bioimpedance measurement is not carried out in excessively superficial areas of the skin;

fourth measuring means suitable for measuring the saturation of hemoglobin present in the peripheral blood of a person, said fourth measuring means comprising at least one emitter suitable for emitting electromagnetic radiations having a wavelength between 600 nm and 1000 nm and at least one receiver suitable for receiving electromagnetic radiation having a wavelength between 600 nm and 1000 nm, said emitter and said receiver being included in said device in such a way that, when said device is in contact with the skin of a person in correspondence with said area of skin, the electromagnetic radiation emitted by said emitter:

impacts against said area at least in correspondence with said first portion of said skin area (of which said microscope is suitable for acquiring an image), i.e., at least in correspondence with the visual field of said microscope and, after having been at least partially reflected and/or dispersed from said first portion of said skin zone, affect, at least partially, against said receiver, when said device is in contact with the skin of a person at said skin area, said fourth measuring means being suitable for calculating the saturation of the hemoglobin present in the peripheral blood in said skin area, at least at said first portion of said area of skin (of which said microscope is suitable for acquiring an image), i.e., at least in correspondence with the visual field of the microscope, by measuring the wavelength of electromagnetic radiations incident against said receiver after being emitted by said emitter and having been reflected and/or dispersed by said first portion of said skin zone (thanks to the fact that the hemoglobin absorbs electromagnetic radiation at different wavelengths depending on whether it is or is not bound to a gas).

The fourth measuring means preferably comprises a pulse oximeter;

a first memory suitable for containing images acquired by said microscope;

a second memory suitable for containing pH values measured by said first measuring means;

a third memory suitable for containing temperature values measured by said second measuring means;

a fourth memory suitable for containing impedance values measured by said third measuring means;

a fifth memory suitable for containing saturation values measured by said fourth measuring means;

means for controlling said microscope, said illuminators and said first, second, third and fourth measuring means, said control means being suitable for memorizing:

in said first memory, images acquired by said microscope;

in said second memory, pH values measured by said first measuring means;

in said third memory, temperature values measured by said second measuring means;

in said fourth memory, impedance values measured by said third measuring means;

in said fifth memory, saturation values measured by said fourth measuring means, said control means being also suitable for combining images acquired by said microscope in correspondence with at least said first portion of said skin area (with said first portion of said skin area corresponding to the visual field of the microscope), when said device is in contact with the skin of a person in correspondence with said area of skin, respectively for storing:

pH values measured by said first measuring means at said second portion of said skin area adjacent to said first portion of said skin area respectively when said images have been acquired;

temperature values measured by said second measuring means at said first portion of said skin area and/or said third portion of said skin area adjacent to said first portion of said skin area, respectively when said images have been acquired;

impedance values measured by said third measuring means at said first portion of said skin region respectively when said images have been acquired;

saturation values measured by said fourth measuring means at said first portion of said skin zone respectively when said images have been acquired;

connection means suitable for establishing a connection between said device and an electronic apparatus for the transmission of data between said control means and said apparatus, when said device is connected to said apparatus by means of said connection means, said control means being suitable for transmitting to said apparatus:

one or more images acquired by said microscope;

one or more pH values measured by said first measuring means;

one or more temperature values measured by said second measuring means;

one or more impedance values measured by said third measuring means;

one or more saturation values measured by said fourth measuring means, when said device is connected to said apparatus by means of said connection means, said control means being also suitable for receiving from said apparatus commands for activating said microscope, said illuminators and said first, second, third and fourth means of measurement.

The device according to the present invention, when applied to an area of the skin of a person, advantageously allows to acquire an image of a first portion of said skin area and at the same time to measure the pH of the skin in a second portion of said skin. skin area adjacent to said first portion of said skin area, to measure the skin temperature at said first portion of said skin area and/or a third portion of said skin area also adjacent to said first portion, of measuring the impedance of body tissues in correspondence with said first portion of said skin zone, and of measuring the saturation of the hemoglobin present in the peripheral blood in said first portion of said skin zone. In other words, the device object of the invention advantageously allows to measure (i.e., to "co-register") the temperature, bioimpedance and saturation of hemoglobin in the field of view of the skin microscope included in the device, and to measure the pH (and possibly the temperature) in the immediate vicinity of said field of view. Thanks to the interaction between the different sensors (and therefore differently from what could be measured by single equipment equipped with one or more sensor each), the device object of the invention allows to define the analysis of the skin of a person by directing them to specific areas and interpolating the results to guide the progress of the measurements. The device therefore allows to obtain an overall picture of the composition of the skin, as well as the state of circulation and the level of perfusion, in the area under observation. As will be illustrated in the following of the present description, by means of the connection means, the device is suitable for indicating to a specialist the stage of the aesthetic-clinical condition of the main possible therapeutic targets. Assuming that the measurements represent a control analysis, these measurements can be compared to what was previously detected, so as to be able to highlight any progress achieved over time. The device is suitable for indicating to a specialist the stage of the aesthetic-clinical condition of the main possible therapeutic targets. Assuming that the measurements represent a control analysis, these measurements can be compared to what was previously detected, so as to be able to highlight any progress achieved over time. The device is suitable for indicating to a specialist the stage of the aesthetic-clinical condition of the main possible therapeutic targets. Assuming that the measurements represent a control analysis, these measurements can be compared to what was previously detected, so as to be able to highlight any progress achieved over time.

The above considerably facilitates a doctor or a cosmetologist in conducting a diagnostic examination of a person's skin. With a single device (object of invention) and in a single measurement it is in fact possible to obtain a better result than what could be obtained not only from the superimposition and subsequent processing of the individual sensors, but also from the combination of much more sophisticated techniques such as low-penetration ultrasound measurements (already difficult to perform in itself), Doppler flowmetry and telethermographic scans (non-integrated methodologies and the cost of many orders of magnitude higher than the device object of the invention).

Other innovative features of the present invention are illustrated in the following description and recalled in the dependent claims.

According to an aspect of the invention, said device comprises at least five of said illuminators, respectively suitable for emitting electromagnetic radiation included in the following five ranges: between 315 nm and 400 nm, between 315 nm and 740 nm, between 500 nm and 650 nm, between 625 nm and 740 nm and between 700 nm and 800 nm.

The illuminators are preferably LEDs.

Illuminators suitable for emitting electromagnetic radiation at a wavelength not exceeding 400 nm (i.e., ultraviolet radiation) advantageously allow to observe fluorescence phenomena.

By comprising the device object of the invention a plurality of illuminators emitting electromagnetic radiations at various wavelengths, the device advantageously allows to diagnose different clinical conditions.

By way of example, through the device object of the invention it is possible to measure the skin roughness of a person by acquiring images of the skin of said person in at least eight areas (including the forehead, lower orbicularis of the eyes, upper masseter and orbicularis of the mouth) emitting, through one or more illuminators, electromagnetic radiation with a wavelength between 400 nm and 700 nm. By acquiring a plurality of images over time, for overlapping areas, it is possible to compare the acquired images in order to evaluate the depth, extension and width of wrinkles, as well as the superficial scaliness and the compactness of the fabric texture. This can also be done in order to evaluate the effectiveness of a therapy or treatment.

Again by way of example, through the device object of the invention it is possible to discriminate a condition of localized adiposity from one of edematous fibro-sclerotic panniculopathy of a person by carrying out numerous repeated acquisitions of the skin of said person, so that the continuous interaction of the temperature sensors, saturation and impedance, as they are gradually delimited by the visual field of the microscope, allows the construction of a distribution map of the surface temperature as well as of the tissue oxygenation in relation to the composition of the tissue. To this end, if, for example, a decrease in the local temperature greater than 0.3° C. is recorded during one of the acquisitions, in the presence of a constant saturation it is possible to measure the percentage of fat mass locally in impedance by comparing it with the value at time zero: if it has increased by more than 0.5%, images of the skin are acquired by emitting electromagnetic radiation through one or more illuminators with a wavelength between 400 nm and 700 nm. If the percentage of fat mass is unchanged, images of the skin are acquired by emitting, through one or more illuminators, both electromagnetic radiation with a wavelength between 315 nm and 400 nm, and electromagnetic radiation with a wavelength between 400 nm and 700 nm. Otherwise, if there is an increase in the local temperature greater than 0.3° C.

Again by way of example, in order to measure the skin hydration of a person, it is necessary to discriminate between the different types of dehydration, including superficial dehydration, deep dehydration, states of real xerosis, dehydration due to loss of the hydro acid film, surface protein type, dehydration due to loss of the integrity of the electrophysiological barrier functions, etc; all this also in relation to local conditions similar to wider clinical pictures and with implications of a different nature, such as seborrheic dermatitis, mycoses and many other dermatoses of various origins. The techniques currently available for measuring skin hydration, even the most complex ones such as corneometry, closed chamber TEWL (Trans Epidermal Water Loss) meters and confocal Raman spectrometers do not allow to obtain sufficiently detailed information about the nature and extent of dehydration. Conversely, by means of the device object of the invention it is possible to measure the impedance in relation to pH measurements and skin imaging, thus being able to identify with unprecedented precision the type, depth and diffusion of dehydration. For this purpose, the device must be positioned on at least three distinct areas of the skin chosen from the forehead, lower orbicularis of the eyes, upper masseter, chin, median sternocleidomastoid area and, possibly, one or two control areas (areas not exposed between subclavicular, median area quadriceps or other), and perform impedance measurements, full spectrum analysis up to at least 1 MHz, pH measurements and skin imaging scans illuminating the area, in sequence, with the entire available wavelength band, for an extension from 315 nm to at least 800 nm. In the face of pH decreases greater than 0.2 units, surface impedance measurements must be made, at depths between 1 mm and 3 mm and between 3 mm and 6 mm. In all cases, by reading the quality parameters of compactness and scaliness of the image of the illuminated skin in the interval between 500 nm and 650 nm, it is possible to obtain the information necessary to differentiate, in particular, superficial dehydration, deep dehydration and dehydration by alteration of the superficial hydro-lipo protein acid film. Otherwise, in the presence of increases in pH greater than 0.2 units, always in the depth ranges mentioned above, it is also possible to integrate images illuminated in white light and in the intervals between 315 nm and 400 nm and between 700 nm and 800 nm, so as to be able to identify also states of physio-pathological xerosis, possibly associated with seborrheic dermatitis and possible fungal infections. At unchanged pH (±0.1 units), especially as a function of the impedance readings at various depths and integrating them with skin imaging in white light and in the range between 500 nm and 650 nm, it is possible to discriminate states of moderate xerosis at superficial and/or deep dehydration, as well as dehydration due to loss of the integrity of the electrophysiological barrier functions. so as to be able to identify also states of physio-pathological xerosis, possibly associated with seborrheic dermatitis and possible fungal infections. At unchanged pH (±0.1 units), especially as a function of the impedance readings at various depths and integrating them with skin imaging in white light and in the range between 500 nm and 650 nm, it is possible to discriminate states of moderate xerosis at superficial and/or deep dehydration, as well as dehydration due to loss of the integrity of the electrophysiological barrier functions so as to be able to identify also states of physio-pathological xerosis, possibly associated with seborrheic dermatitis and possible fungal infections. At unchanged pH (±0.1 units), especially as a function of the impedance readings at various depths and integrating them with skin imaging in white light and in the range between 500 nm and 650 nm, it is possible to discriminate states of moderate xerosis at superficial and/or deep dehydration, as well as dehydration due to loss of the integrity of the electrophysiological barrier functions.

According to another aspect of the invention, said illuminators are arranged at least partially around the optics of said microscope, each of said illuminators being oriented in such a way that, when said illuminator emits electromagnetic radiations, said electromagnetic radiations are emitted away from the optics of said microscope.

According to another aspect of the invention, said illuminators are arranged circumferentially around the optical axis of said microscope, and are angularly equidistant from each other.

According to this aspect of the invention, schematizing the illuminators as point sources, the illuminators are arranged on a circumference arranged orthogonally to the optical axis of the microscope and having the center on said optical axis. The arcs of said circumference, each of which having as ends respectively an illuminator and the illuminator immediately preceding or following it, are also equal to each other.

According to another aspect of the invention, said first measuring means are included in said device in such a way that, when said device is in contact with the skin of a person in correspondence with said area of skin, said first measuring means are suitable for measuring the pH of the skin of said person at least in correspondence with a point of an edge delimiting said first portion of said area of skin (of which said microscope is suitable for acquiring an image), i.e., on the border of the visual field of the microscope, extremely close to the aforementioned first portion of the skin area, said edge being at least partially common to said second portion of said skin area (adjacent to said first portion of said skin area at least in correspondence with which said microscope is suitable for acquiring an image of the skin).

According to another aspect of the invention, said first measuring means are included in said device in such a way that, when said device is in contact with the skin of a person in correspondence with said area of skin, said first measuring means are suitable for measuring the pH of the skin of said person in a plurality of points of said edge (delimiting said first portion of said skin area of which said microscope is suitable for acquiring an image), said first measuring means being furthermore suitable for carrying out an average of the pH values respectively measured in said plurality of points of said edge so as to estimate the pH of the skin of said person in correspondence with said first portion of said area of skin (of which said microscope is suitable for acquiring an image), i.e., in correspondence with the visual field of the microscope), said average of pH values being memorable in said second memory, combinable with an image acquired by said microscope and transmissible to said apparatus in place of a pH value measured by said first measuring means.

Advantageously, according to this aspect of the invention, even if the pH of the skin is not measured directly in the visual field of the microscope, the pH is measured in such a way as to be able to interpolate what the aforementioned detection would have been if it had been carried out in the visual field of the microscope. microscope.

According to another aspect of the invention, said second measuring means are included in said device in such a way that, when said device is in contact with the skin of a person in correspondence with said area of skin, said second measuring means are suitable for measuring the temperature of the skin of said person at least in correspondence with a point of an edge delimiting said first portion of said area of skin (of which said microscope is suitable for acquiring an image), i.e., on the border of the visual field of the microscope, extremely close to the aforementioned first portion of the skin area taken by the microscope, said edge at a point of which said second measuring means are suitable for measuring the temperature of the skin of said person, being at least partially common to said third portion of said skin area (adjacent to said first portion of said skin area at least in correspondence with which said second measuring means are suitable for measuring the temperature of the skin of said person).

According to another aspect of the invention, said second measuring means are included in said device in such a way that, when said device is in contact with the skin of a person in correspondence with said area of skin, said second measuring means are suitable for measuring the temperature of the skin of said person in a plurality of points of said edge at least partially common to said third portion of said skin zone, said second measuring means being furthermore suitable for carrying out an average of the temperature values respectively measured in said plurality of points of said edge at least partially common to said third portion of said skin zone, so as to estimate the temperature of the skin of said person in correspondence with said first portion of said skin zone (of which said microscope is suitable for acquiring an image), i.e., in correspondence with the visual field of the microscope), said average of temperature values being memorable in said third memory, combinable with an image acquired by said microscope and transmissible to said apparatus in place of a temperature value measured by said second measuring means.

Advantageously, according to this aspect of the invention, even if the skin temperature is not measured directly in the visual field of the microscope, the temperature is measured in such a way as to be able to interpolate what the aforementioned detection would have been if it had been carried out in the visual field of the microscope.

According to another aspect of the invention, said second measuring means comprise an infrared electromagnetic radiation thermometer, said thermometer being included in said device in such a way that, when said device is in contact with the skin of a person in correspondence with said area of skin, said thermometer is suitable for receiving infrared electromagnetic radiation irradiated by said first portion of said area of skin (of which said microscope is suitable for acquiring an image), so as to be suitable for measuring the temperature of the skin of said person in correspondence with said first portion of said area of skin (of which said microscope is suitable for acquiring a image), i.e., at least in correspondence with the field of view of the microscope).

According to another aspect of the invention, said measuring thirds, when said device is in contact with the skin of a person in correspondence with said skin area, are suitable for applying, through said pair of electrodes, to body tissues included in said skin area at least in correspondence with said first portion of said skin area (of which said microscope is suitable for acquiring an image), i.e., included in said skin area at least in correspondence with the visual field of the microscope, potential differences such as wherein said alternating electric current flowing through said body tissues following the application of said potential differences thereto, crosses said body tissues in two or more frequency ranges each between 1 kHz and 1 MHz.

According to another aspect of the invention, said emitter of said fourth measuring means and said receiver of said fourth measuring means lie on opposite sides with respect to the optics of said microscope (so that the visual field of the microscope is interposed between said emitter and receiver), said emitter being oriented in such a way that when said emitter emits electromagnetic radiations, said electromagnetic radiations are emitted away from the optics of said microscope.

According to another aspect of the invention, said receiver of said fourth measuring means is housed inside the optics of said microscope.

According to another aspect of the invention, said control means comprise first algorithms for the determination of values respectively assumed by first characteristic parameters of images acquired by said microscope, said control means, by means of said first algorithms, being suitable for:

receiving as input data one of said images acquired by said microscope it's at calculate values assumed by said first parameters and associated with said input image, said device comprising a sixth memory suitable for containing values assumed by said first parameters and calculated by said control means by means of said first algorithms, said control means being suitable for storing in said sixth memory values assumed by said first parameters and calculated by means of said first algorithms, said control means being furthermore suitable for combining values assumed by said first parameters and calculated by means of said first algorithms by receiving in input one of said images acquired by said microscope in correspondence with at least said first portion of said skin area (with said first portion of said area of skin corresponding to the field of view of the microscope), when said device is in contact with the skin of a person in correspondence with said area of skin, to:

said pH value combined with said image (i.e., measured by said first measuring means at said second portion of said skin area when said image has been acquired) or to said average of pH values, if it can be carried out by said first measuring means, combined with said image;

said temperature value combined with said image (i.e., measured by said second measuring means at said first portion of skin area and/or said third portion of said skin area when said image has been acquired)

or to said average of temperature values, if it can be carried out by said second measuring means, combined with said image;

said impedance value combined with said image (i.e., measured by said third measuring means at said first portion of said skin area when said image has been acquired);

said saturation value combined with said image (i.e., measured by said fourth measuring means at said first portion of said skin area when said image has been acquired), in other words, said control means being suitable for combining values assumed by said first parameters and associated with one of said images acquired by said microscope, to:

said pH value combined with said image or said average of pH values, if it can be carried out by said first measuring means, combined with said image;

said temperature value combined with said image or said average of temperature values, if it can be carried out by said second measuring means, combined with said image;

said impedance value coupled to said image;

said saturation value combined with said image, when said device is connected to said apparatus by means of said connection means, said control means being suitable for transmitting to said apparatus one or more values assumed by said first parameters and calculated by means of said first algorithms.

The first algorithms may comprise an expert system and/or a numerical classifier with a training system supervising the same.

The first parameters can be organized in a "feature vector" and consist, by way of example, in estimates of empirical characteristics such as roughness, pigmentation and hydration.

According to another aspect of the invention, said control means comprise second algorithms for the determination of values respectively assumed by second characteristic parameters of said first portion of said skin area at least in correspondence with which said microscope is suitable for acquiring images of said skin when said device is in contact with said skin in correspondence of said zone, said control means, by means of said second algorithms, being suitable for:

receive as input data:

values assumed by said first parameters and calculated by said control means through said first algorithms receiving in input one of said images acquired by said microscope in correspondence with at least said first portion of said skin area (with said first portion of said skin area corresponding to the visual field of the microscope), when said device is in contact with said skin in correspondence with said zone and said pH value combined with them (i.e., measured by said first measuring means in correspondence with said second portion of said skin area when said image has been acquired)

or said average of pH values, if it can be carried out by said first measuring means, combined thereto;

said temperature value combined with them (i.e., measured by said second measuring means at said first portion of said skin area and/or said third portion of said skin area when said image has been acquired)

or said average of temperature values, if it can be carried out by said second measuring means, coupled thereto;

said impedance value coupled thereto (i.e., measured by said third measuring means at said first portion of said skin area when said image has been acquired);

said saturation value combined with them (i.e., measured by said fourth measuring means in correspondence with said first portion of said skin area when said image has been acquired)

and for:

calculating values assumed by said second parameters and associated with said image (to which said values assumed by said first parameters and received at the input are in turn associated), said device comprising a seventh memory suitable for containing values assumed by said second parameters and calculated by said control means by means of said second algorithms, said control means being suitable for storing in said seventh memory values assumed by said second parameters and calculated by means of said second algorithms, when said device is connected to said apparatus by means of said connection means, said control means being suitable for transmitting to said apparatus one or more values assumed by said second parameters and calculated by means of said second algorithms.

Like the first algorithms, the second algorithms can comprise an expert system and/or a numerical classifier with a training system supervising the same.

The second parameters consist, by way of example, in so-called "fuzzy" estimates of the level of agreement of the first parameters with what is expected for specific pathological conditions.

Another object of the invention is a system for conducting a multiparametric examination of the skin of a person, said system comprising:

one or more devices object of the invention;

for each of said devices, said electronic device, such as for example a "smartphone", connectable to said device for transmitting data between said device and said control means of said device, by means of said connection means of the latter;

a server, each of said apparatus being suitable for establishing a connection with said server for the transceiving of data between said apparatus and said server, each of said devices, when connected to said server, being also suitable for transmitting to the latter (i.e., to said server):

one or more images acquired by said microscope of said device connectable to said apparatus and received by said apparatus by said device when connected (said device) to said apparatus;

one or more pH values measured by said first measuring means of said device, or one or more said pH value averages, if these can be carried out by said first measuring means of said device, connectable to said device and received by said device from part of said device when connected (said device) to said device;

one or more temperature values measured by said second measuring means of said device, or one or more said temperature value averages, if these can be carried out by said second measuring means of said device, connectable to said device and received by said device from part of said device when connected (said device) to said device;

one or more impedance values measured by said third measuring means of said device connectable to said apparatus and received by said apparatus by said device when connected (said device) to said apparatus;

one or more saturation values measured by said fourth measuring means of said device connectable to said apparatus and received by said apparatus by said device when connected (said device) to said apparatus and/or if said control means of said devices comprise said first algorithms, one or more values assumed by said first parameters and calculated by said control means, through said first algorithms, of said device connectable to said device and received by said device by said device when connected (said device) to said device and/or if said control means of said devices comprise said second algorithms, one or more values assumed by said second parameters and calculated by said control means, through said second algorithms, of said device connectable to said device and received by said device by said device when connected (said device) to said device, for each of said devices, said server being suitable for storing:

said one or more images received from said server by said apparatus when connected (said apparatus) to said server;

said one or more pH values, or said one or more averages of pH values, received from said server by said apparatus when connected (said apparatus) to said server;

said one or more temperature values, or said one or more averages of temperature values, received from said server by said appliance when connected (said appliance) to said server;

said one or more impedance values received from said server by said apparatus when connected (said apparatus) to said server;

said one or more saturation values received from said server by said appliance when connected (said appliance) to said server, and/or if said control means of said devices comprise said first algorithms, said one or more values assumed by said first parameters and received from said server by said device when connected (said device) to said server and/or if said control means of said devices comprise said second algorithms, said one or more values assumed by said second parameters and received from said server by said device when connected (said device) to said server.

The server advantageously allows storing data acquired from multiple devices object of the invention, for example in order to allow a doctor or a cosmetologist to access them, so as to be able to carry out a remote analysis of the skin conditions and possibly verify the progress of therapies or treatments performed.

BRIEF DESCRIPTION OF THE DRAWINGS

Further objects and advantages of the present invention will become clear from the following detailed description of examples of embodiment of the same and from the attached drawings, given purely for explanatory and non-limiting purposes, in which.

DETAILED DESCRIPTION

In the remainder of the present description, a figure may also be illustrated with reference to elements not expressly indicated in that figure but in other figures. The scale and proportions of the various elements depicted do not necessarily correspond to the real ones.

Figure 1:
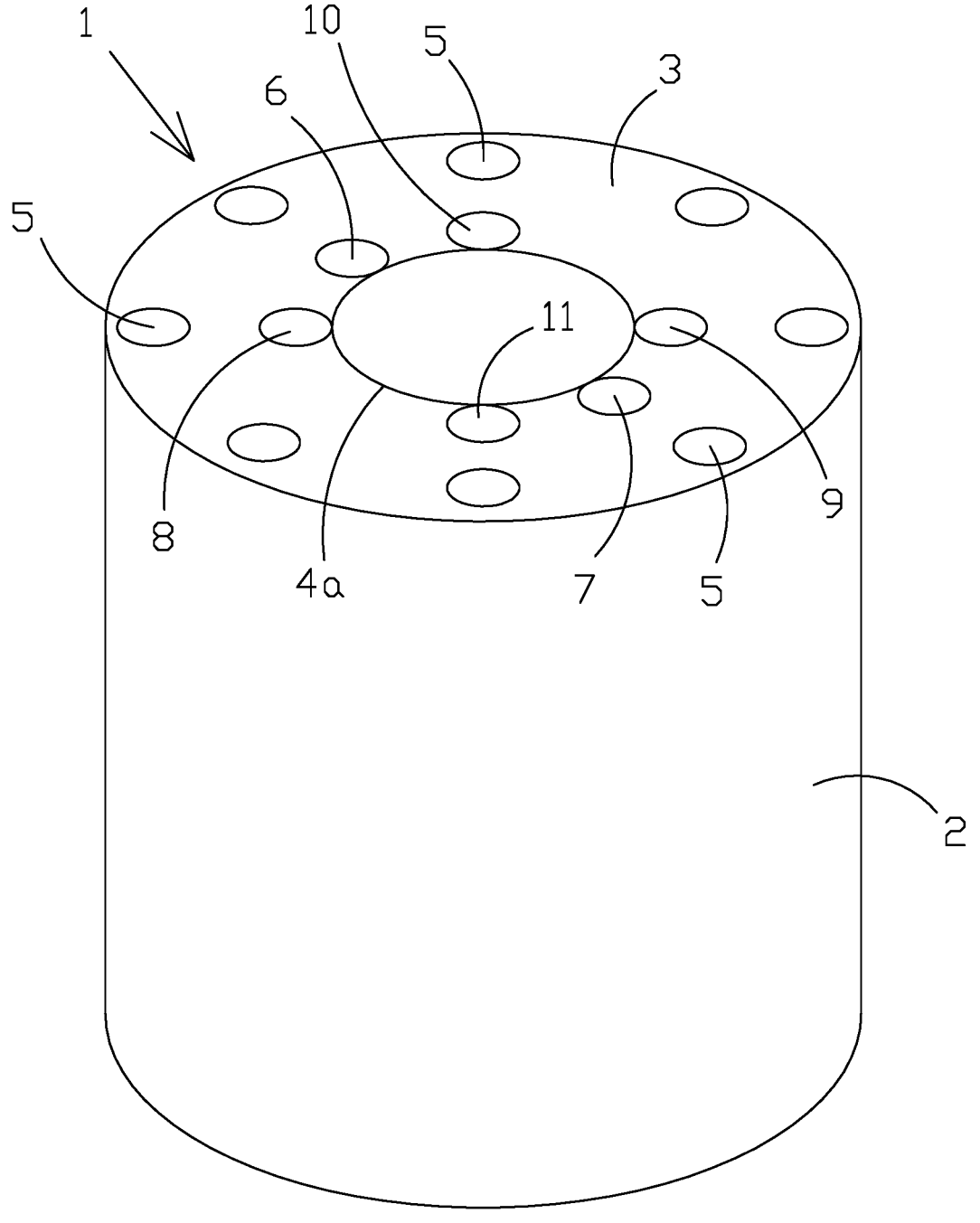
FIG. 1 shows, in a schematic perspective view, a device according to the present invention.

FIG. 1 shows a device 1, object of the invention, for conducting a multiparametric examination of human skin.

The device 1 comprises a support structure 2 in correspondence with which said device 1 can be grasped by a person. By way of example, the structure 2 is shaped as a substantially cylindrical straight casing and the device 1 can be grasped preferably at the lateral surface of the structure 2. More precisely, the device 1 can be grasped by a person in order to bring said device 1 to contact with your skin in correspondence with an area of the latter to be examined. Again by way of example, the device 1 can be worn in contact with an area of the skin of a person in correspondence with one of the two substantially circular bases of the structure 2.

Figure 2:
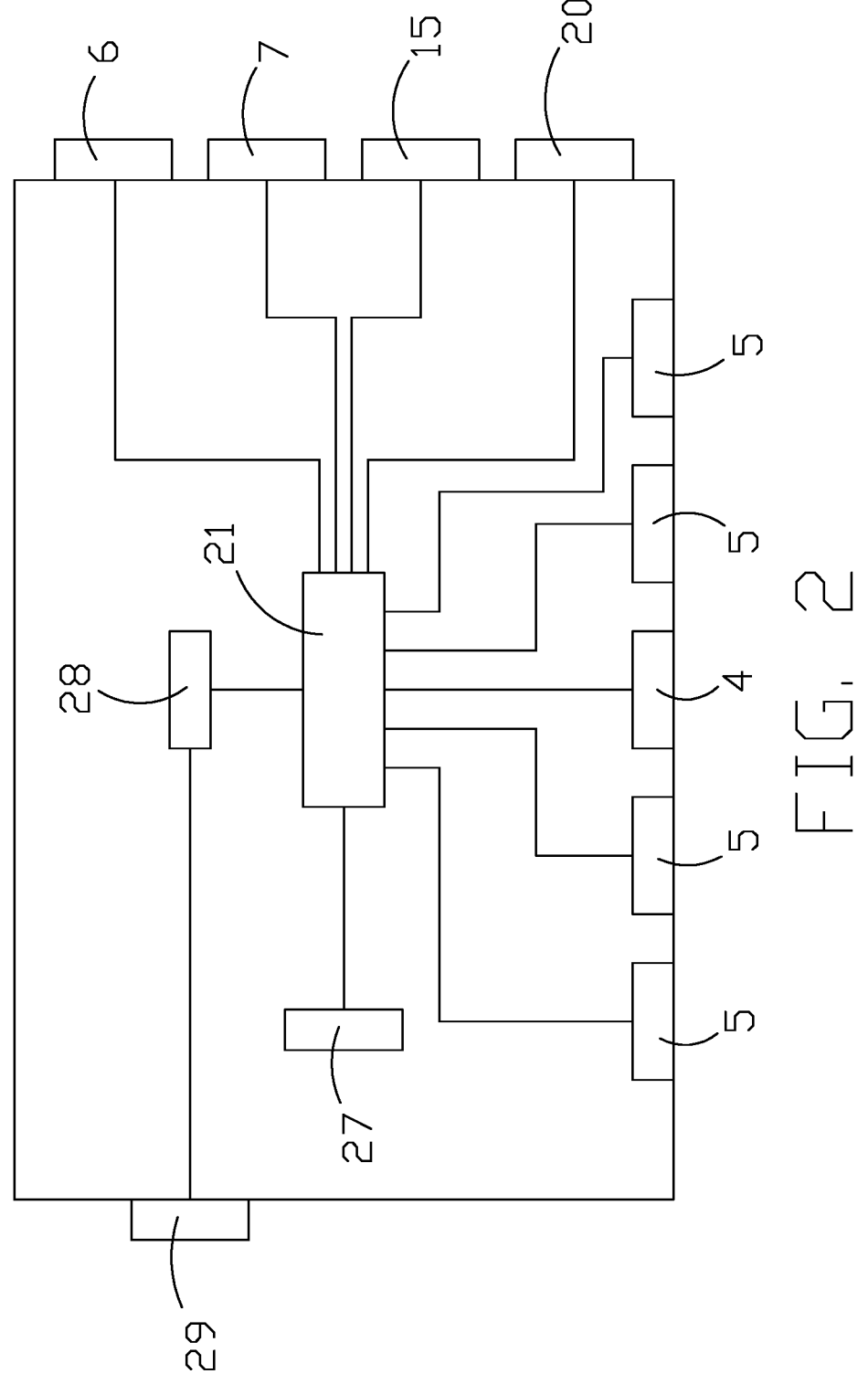
FIG. 2 schematically shows some components of the device of FIG. 1 and the way in which said components interact with each other.
Figure 3:
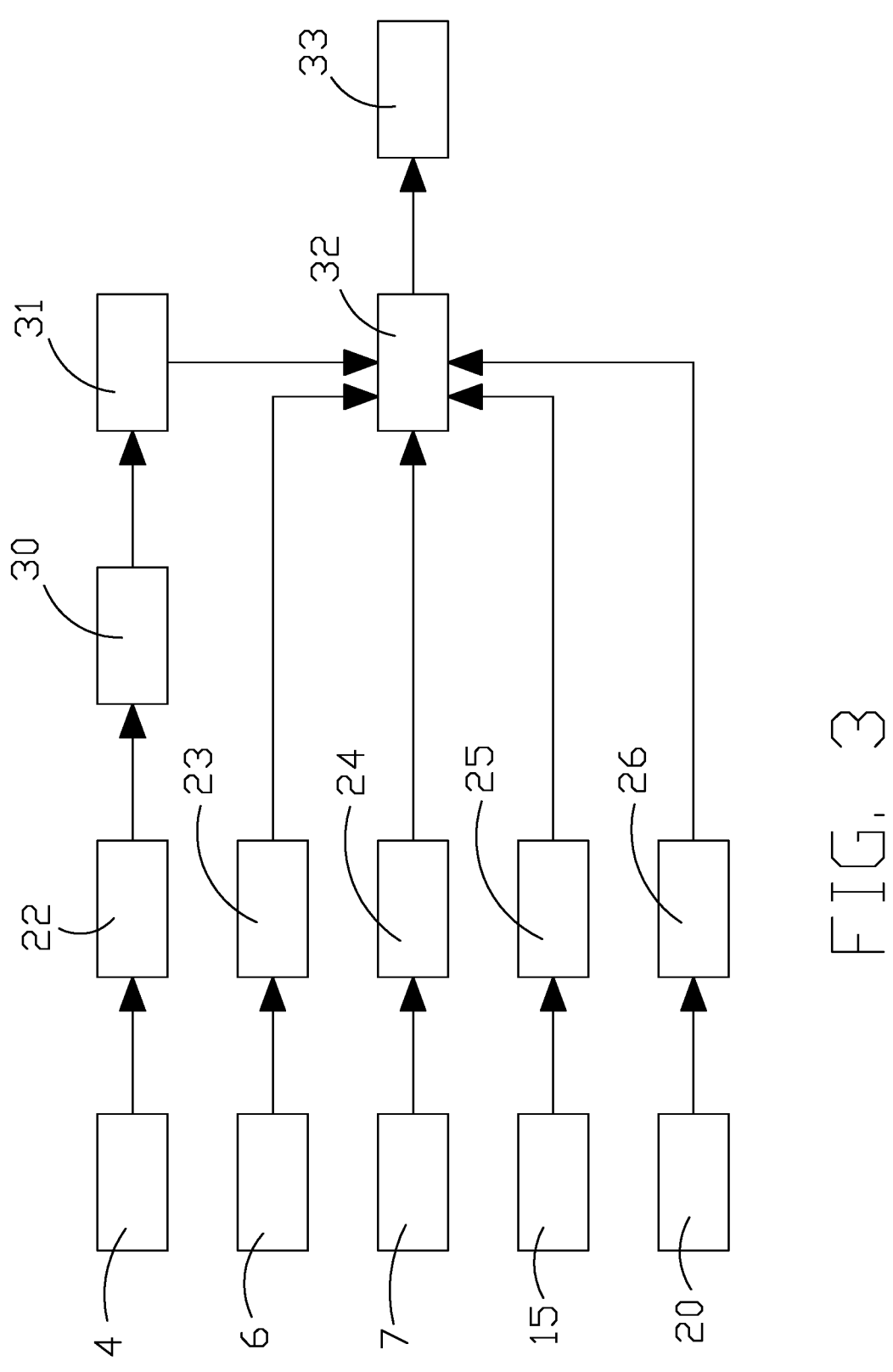
FIG. 3 schematically shows further components of the device of FIG. 1 and the way in which said further components interact with each other.

The device 1 includes a skin microscope 4 (shown schematically in FIGS. 2 and 3) whose optics 4a is preferably fixed focus, with a structure preferably comprising from three to five lenses. The microscope 4 is included in the device 1 in such a way that, when the device 1 is in contact with the skin of a person in correspondence with an area of said skin, the microscope 4 is suitable for acquiring an image of at least a first portion of said skin area. Incidentally, said first portion of said skin area (of which the microscope 4 is suitable for acquiring an image) corresponds to the visual field of the microscope 4. The optic 4a is preferably in correspondence with the base 3.

The device 1 further comprises a plurality of illuminators 5, each of which is suitable for emitting electromagnetic radiations in at least one wavelength range. The illuminators 5 are included in the device 1 in such a way that, when the device 1 is in contact with the skin of a person in correspondence with said skin area, the electromagnetic radiations emitted by the illuminators 5 strike against said skin area at least in correspondence with said first portion of said skin zone of which the microscope 4 is suitable for acquiring an image (i.e., at least in correspondence with the visual field of the microscope 4) and, after having been at least partially reflected and/or dispersed by said first portion of said skin area, at least partially affect the optic 4a.

The illuminators 5 are preferably LEDs and each of them is preferably suitable for emitting electromagnetic radiations having a wavelength of not less than 100 nm and not more than 1 mm. That is, each of the illuminators 5 is preferably suitable for emitting infrared radiations and/or ultraviolet radiations and/or radiations belonging to the visible spectrum. More preferably, the device 1 comprises at least five illuminators respectively suitable for emitting electromagnetic radiations included in the following five ranges:

between 315 nm and 400 nm, between 315 nm and 740 nm, between 500 nm and 650 nm, between 625 nm and 740 nm and between 700 nm and 800 nm.

The illuminators 5 are preferably arranged, at least partially, around the optic 4a and, incidentally, are oriented in such a way that, when an illuminator 5 emits electromagnetic radiations, said electromagnetic radiations are emitted away from the optic 4a. More preferably, the illuminators 5 are arranged circumferentially around the optical axis of the microscope 4, and are angularly equidistant from each other.

The device 1 comprises a first sensor 6 suitable for measuring the pH of the skin when in contact with the latter. The sensor 6, falling within the aforementioned "first measuring means", is included in the device 1 in such a way that, when the device 1 is in contact with the skin of a person in correspondence with said area of skin, the sensor 6 is in contact with the skin of said person, so as to measure its pH, at least in correspondence with a second portion of said skin area adjacent to said first portion of said skin area of which the microscope 4 is suitable for acquiring an image (i.e., at least in correspondence with a second portion of said area of skin adjacent to the visual field of the microscope 4). As can be seen in FIG. 1, the sensor 6 is preferably in correspondence with the base 3, more preferably in a position extremely close to the optic 4a. In particular, the sensor 6 is included in the device 1 preferably in such a way that, when the device 1 is in contact with said area of skin, the sensor 6 is in contact with the skin of said person, so as to measure its pH, at least in correspondence with a point of the border delimiting said first portion of said skin area of which the microscope 4 is suitable for acquiring an image (i.e., on the border of the visual field of the microscope 4, extremely close to the aforementioned first portion of the skin area taken from the microscope 4). Incidentally, the aforementioned edge is at least partially common to the aforementioned second portion of said skin area adjacent to said first portion of said skin area.

According to a variant of the device 1, the latter comprises a plurality of sensors 6 included in said device 1 preferably in such a way that, when the device 1 is in contact with the aforementioned area of skin, the sensors 6 are in contact with the skin of said person, so as to measure its pH, respectively in a plurality of points of the aforementioned edge delimiting said first portion of said skin area of which the microscope 4 is suitable for acquiring an image. More preferably, the aforementioned second portion of said skin zone surrounds the optics 4a of the microscope 4 and the sensors 6, like the illuminators 5, are therefore arranged, at least partially, around the optics 4a. Even more preferably, the sensors 6 are arranged circumferentially around the optical axis of the microscope 4, and are angularly equidistant to each other.

According to this variant of the device 1, the sensors 6 are suitable to carry out, or allow the carrying out of, a preferably weighted average of the pH measurements respectively carried out in the aforementioned plurality of points of the aforementioned edge, so as to estimate the pH of the skin of said person in correspondence with said first portion of said skin area of which the microscope 4 is suitable for acquiring an image (i.e., in correspondence with the visual field of the microscope 4). Even if the pH of the skin is not measured directly in the visual field of the microscope 4, the pH is therefore measured in such a way as to be able to interpolate what the above detection would have been if it had been carried out in said visual field.

The device 1 comprises a second sensor 7 suitable for measuring the temperature of the skin when in contact with the latter. The sensor 7, falling within the aforementioned "second measuring means", is included in the device 1 in such a way that when the device 1 is in contact with the skin of a person in correspondence with said area of skin, the sensor 7 is in contact with the skin of the skin of said person, so as to measure its temperature, at least in correspondence with a third portion of said skin area adjacent to said first portion of said skin area of which the microscope 4 is suitable for acquiring a image (i.e., at least in correspondence with a third portion of said area of skin adjacent to the visual field of the microscope 4). As can be seen in FIG. 1, the sensor 7 is preferably in correspondence with the base 3, more preferably in a position extremely close to the optic 4a. In particular, the sensor 7 is included in the device 1 preferably in such a way that, when the device 1 is in contact with said area of skin, the sensor 7 is in contact with the skin of said person, so as to measure its temperature, at least in correspondence with a point of the border delimiting said first portion of said skin area of which the microscope 4 is suitable for acquiring an image (i.e., on the border of the visual field of the microscope 4, extremely close to the aforementioned first portion of the skin area taken from the microscope 4). Incidentally, the aforementioned edge is at least partially common also to the aforementioned third portion of said skin area adjacent to said first portion of said skin area. That is, the aforementioned edge separates, at least partially, the aforementioned third portion of said area of said skin from said first portion of said skin area. By way of example and as shown in FIG. 1, the sensors 6 and 7 are diametrically opposite with respect to the optics 4a of the microscope 4.

According to a variant of the device 1, the latter comprises a plurality of sensors 7 included in said device 1 preferably in such a way that, when the device 1 is in contact with the aforementioned area of skin, the sensors 7 are in contact with the skin of said person, so as to measure their temperature, respectively in a plurality of points of the aforementioned edge delimiting said first portion of said skin area of which the microscope 4 is suitable for acquiring an image. More preferably, the aforementioned third portion of said skin zone surrounds the optics 4a of the microscope 4 and the sensors 7, like the illuminators 5, are therefore arranged, at least partially, around the optics 4a. Even more preferably, the sensors 7 are arranged circumferentially around the optical axis of the microscope 4, and are angularly equidistant from each other. Incidentally, the aforementioned third portion of said skin area could coincide with, or be partially superimposed on, the aforementioned second portion of said skin area.

According to this variant of the device 1, the sensors 7 are suitable for carrying out, or allowing for the carrying out of, a preferably weighted average of the temperature measurements respectively carried out in the aforementioned plurality of points of the aforementioned edge so as to estimate the temperature of the skin of said person in correspondence with said first portion of said skin zone of which the microscope 4 is suitable for acquiring an image (i.e., in correspondence with the visual field of the microscope 4). Even if the skin temperature is not measured directly in the visual field of the microscope 4, the temperature is therefore measured in such a way as to be able to interpolate what the above detection would have been if it had been carried out in said visual field.

By way of example, if the device object of the invention comprises both a plurality of sensors 6 and a plurality of sensors 7 as described above respectively, and the sensors 6 are equal in number to the sensors 7, the sensors 6 and 7 are preferably arranged circumferentially around the optical axis of the microscope 4 and in such a way that the sensors 6 are alternated with the sensors 7.

According to another variant of the device 1, the sensor 7 comprises an infrared electromagnetic radiation thermometer, so as to be able to detect the temperature of the skin without having to come into contact with the latter. The aforementioned thermometer is included in the device 1 in such a way that, when the device 1 is in contact with the skin of a person in correspondence with said area of the skin, the infrared electromagnetic radiation thermometer is suitable for measuring the temperature of the skin at least in correspondence with said first portion of said skin zone of which the microscope 4 is suitable for acquiring an image (i.e., at least in correspondence with the visual field of the microscope 4).

The device 1 comprises a third sensor 15 (shown schematically in FIGS. 2 and 3) suitable for measuring the impedance of body tissues of a person. The sensor 15, falling within the aforementioned "third measuring means", is included in the device 1 in such a way that, when the device 1 is in contact with the skin of a person in correspondence with said area of skin, the sensor 15 is suitable for measuring the impedance of body tissues included in said zone, at least in correspondence with said first portion of said skin zone of which the microscope 4 is suitable for acquiring an image (i.e., at least in correspondence with the visual field of the microscope 4). Going into more detail, the sensor 15 comprises at least a pair of electrodes 8 and 9 included in the device 1 in such a way that, when the device 1 is in contact with the skin of a person in correspondence with said area of said skin, the electrodes 8 and 9 are in contact with the skin of said person respectively on opposite sides with respect to said first portion of said skin area of which the microscope 4 is suitable for acquiring an image (so that the visual field of the microscope is interposed between said electrodes). As can be seen in FIG. 1, the electrodes 8 and 9, like the sensors 6 and 7, are preferably in correspondence with the base 3, more preferably in a position extremely close to the optics 4a. In particular, the electrodes 8 and 9 are included in the device 1 preferably in such a way that, when the device 1 is in contact with said area of skin, the electrodes 8 and 9 are in contact with the skin of said person in correspondence with two respective mutually opposite points of the border delimiting said first portion of said skin area of which the microscope 4 is suitable for acquiring an image (i.e., on the border of the visual field of the microscope 4, extremely close to the aforementioned first portion of the skin area imaged from the microscope 4).

The sensor 15 is suitable for applying a potential difference between the electrodes 8 and 9. More precisely, when the device 1 is in contact with the skin of a person in correspondence with said area of skin, the sensor 15 is suitable for calculating the impedance of body tissues included in said zone, at least in correspondence with said first portion of said skin zone of which said microscope is suitable for acquiring an image (i.e., at least in correspondence with the visual field of the microscope), by measuring a alternating electric current flowing through said body tissues following the application to them of a potential difference through the electrodes 8 and 9. Preferably, the potential difference applied to said body tissues through the electrodes 8 and 9 is such that the alternating electric current flowing through said body tissues following the application of said potential difference thereto, crosses said body tissues in two or more intervals of frequencies each between 1 kHz and 1 MHz.

In light of the foregoing, the sensor 15 makes it possible to measure the bioimpedance of the skin in the visual field of the microscope 4 as a function of the applied frequency. Since the body tissues have different bioimpedance characteristics, the sensor 15 is suitable for carrying out, or allowing the carrying out of, a weighted average of the tissue composition in the visual field of the microscope 4.

The device 1 also comprises a fourth sensor 20 (shown schematically in FIGS. 2 and 3) suitable for measuring the saturation of the hemoglobin present in the peripheral blood of a person. The sensor 20, preferably corresponding to an oximeter (also known as a "pulse oximeter") and falling within the aforementioned "fourth measuring means", is included in the device 1 in such a way that, when the device 1 is in contact with the skin of a person in correspondence with said skin zone, the sensor 20 is suitable for measuring the saturation of hemoglobin present in the peripheral blood of said zone, at least in correspondence with said first portion of said skin zone for which the microscope 4 is suitable to acquire an image (i.e., at least in correspondence with the visual field of the microscope 4). Going into more detail, the sensor 20 comprises at least one emitter 10 suitable for emitting electromagnetic radiations having a wavelength between 600 nm and 1000 nm and at least one receiver 11 suitable for receiving electromagnetic radiations having a wavelength between 600 nm and 1000 nm. The emitter 10 preferably comprises two transmitter LEDs, one red and one infrared. The receiver 11 preferably comprises a receiving photodiode. The emitter 10 and the receiver 11 are included in the device 1 in such a way that, when the device 1 is in contact with the skin of a person in correspondence with said area of skin, the electromagnetic radiations emitted by the emitter 10 strike against said zone at least in correspondence with said first portion of said skin zone of which the microscope 4 is suitable for acquiring an image (i.e., at least in correspondence with the visual field of said microscope) and, after having been at least partially reflected and/or dispersed by said first portion of said skin area, they strike, at least partially, against the receiver 11. As can be seen in FIG. 1, the emitter 10 and the receiver 11, like the electrodes 8 and 9 and sensors 6 and 7 are preferably at the base 3, more preferably in a position extremely close to the optic 4a. Even more preferably, the emitter 10 and the receiver 11 are diametrically opposite with respect to the optic 4a and the emitter 10, incidentally, is oriented in such a way that, when it emits electromagnetic radiation, the latter are emitted away from the optic 4a.

When the device 1 is in contact with the skin of a person in correspondence with the aforementioned area of skin, the sensor 20 is suitable for calculating the saturation of the hemoglobin present in the peripheral blood in said area, at least in correspondence with said first portion of said area skin area of which said microscope is suitable for acquiring an image (i.e., at least in correspondence with the visual field of the microscope), by measuring the wavelength of electromagnetic radiation incident against the receiver 11 after being emitted by the emitter 10 and have been reflected and/or dispersed from said first portion of said skin zone.

According to a variant of the device 1, the receiver 11 is housed inside the optic 4a.

The device 1 comprises a microprocessor (or a microcontroller) 21 connected to the microscope 4, to the illuminators 5 and to the sensors 6, 7, 15 and 20 to control the operation of these components 4, 5, 6, 7, 15 and 20. The microprocessor 21 falls within the aforementioned "control means".

The device 1 also includes: a first memory 22 suitable for containing the images acquired by the microscope 4, a second memory 23 suitable for containing the pH values measured by the sensor 6, a third memory 24 suitable for containing the temperature values measured by the sensor 7, a fourth memory 25 suitable for containing the impedance values measured by the sensor 15 and a fifth memory 26 suitable for containing the saturation values measured by the sensor 20.

Incidentally, if the device 1 comprises a plurality of sensors 6, the pH values that can be entered in the memory 23 may correspond to the pH measurements carried out by the individual sensors 6 and/or to the averages of said pH measurements carried out by the sensors 6.

Again incidentally, if the device 1 comprises a plurality of sensors 7, the temperature values that can be entered in the memory 24 may correspond to the temperature measurements made by the individual sensors 7 and/or to the averages of said temperature measurements made by the sensors 7.

The microprocessor 21 is also connected to the memories 22, 23, 24, 25 and 26 and is suitable for storing the images acquired by the microscope 4 in the memory 22, the pH values measured by the sensor 6 (and/or the pH values measured by the plurality of sensors 6, if present, and/or the averages of said pH values) in the memory 23, the temperature values measured by the sensor 7 (and/or the temperature values measured by the plurality of sensors 7, if present, and/or the averages of said temperature values) in the memory 24, the impedance values measured by the sensor 15 in the memory 25 and the saturation values measured by the sensor 20 in the memory 26.

The microprocessor 21 is also suitable for combining images acquired by the microscope 4 in correspondence with at least said first portion of said skin area of a person (with said portion of said skin area corresponding to the visual field of the microscope 4), when the device 1 is in contact with said skin in correspondence of said area, respectively to:

pH values measured by the sensor 6 (and/or the pH values measured by the plurality of sensors 6, if present, and/or the averages of said pH values) at said second portion of said skin zone respectively when said images have been acquired;
temperature values measured by the sensor 7 (and/or the temperature values measured by the plurality of sensors 7, if present, and/or the averages of said temperature values) in correspondence with said first portion of said area of skin and/or said third portion of said skin zone respectively when said images have been acquired;
impedance values measured by the sensor 15 in correspondence with said first portion of said skin zone respectively when said images have been acquired;
saturation values measured by the sensor 20 in correspondence with said first portion of said skin zone respectively when said images have been acquired.

The device 1 is preferably equipped with an electric accumulator 28 for powering the microscope 4, the illuminators 5, the sensors 6, 7, 15 and 20 and the microprocessor 21. The device 1 can also be connected to an electronic device, such as for example a smartphone, for transmitting data between the microprocessor 21 and said apparatus. This connection can take place via cable and/or through the transceiving of radio frequency electromagnetic waves. In order to allow a connection via cable, the device 1 preferably comprises a micro-USB port 29. In order to allow a connection by means of the transceiver of radio frequency electromagnetic waves, the device 1 preferably comprises an antenna 27 suitable for allowing a connection via Bluetooth or via a WiFi network.

When the device 1 is connected to the aforementioned apparatus through the port 29 and/or the antenna 27, the microprocessor 21 is suitable for transmitting to said apparatus the images acquired by the microscope 4, the pH values measured by the sensor 6 (and/or pH values measured by the plurality of sensors 6, if present, and/or the averages of said pH values), the temperature values measured by the sensor 7 (and/or the temperature values measured by the plurality of sensors 7, if present, and/or the averages of said temperature values), the impedance values measured by the sensor 15 and the saturation values measured by the sensor 20.

When the device 1 is connected to said apparatus by means of the port 29 or the antenna 27, the microprocessor 21 is also suitable for receiving from said apparatus activation commands for the microscope 4, the illuminators 5 and the sensors 4, 6, 7, 15 and 20.

In light of the foregoing, the images acquired by the microscope 4 and the pH, temperature, impedance and saturation values respectively associated with them (as specified above, i.e., "co-registered") can be transmitted from device 1 to a smartphone (for example in the possession of the person who used the device 1). From said smartphone, said images and said values associated with them can be easily forwarded to another person, such as for example a specialist, such as a doctor or a cosmetologist. The device 1 can be controlled by means of said smartphone connectable to it, for example by means of a suitable "app".

The microprocessor 21 could comprise first algorithms 30 for determining the values respectively assumed by the first characteristic parameters of images acquired by the microscope 4. The microprocessor 21, by means of the algorithms 30, is in this case suitable for:

receiving as input data one of the images acquired by the microscope 4 and stored in the memory 22
and for
calculating values assumed by said first parameters and associated with the image received at the input.

If the microprocessor 21 comprises the algorithms 30, the device 1 comprises a sixth memory 31 suitable for containing the values assumed by said first parameters and calculated by the microprocessor 21 through said first algorithms. The microprocessor 21 is also suitable for storing in the memory 31 values assumed by said first parameters and calculated by means of the algorithms 30, and to combine the values assumed by said first parameters and calculated by means of the algorithms 30, receiving in input one of the images acquired by the microscope 4 at at least said first portion of said skin area of a person (with said first portion of said skin area corresponding to the visual field of the microscope 4), when the device 1 is in contact with said skin at said area, to the pH value combined with said image (i.e., measured by sensor 6 in correspondence with said second portion of said skin area, adjacent to said first portion of said skin area, when said image has been acquired) or to the average of pH values, if a plurality of sensors 6 is present, combined with said image;
temperature value combined with said image (i.e., measured by sensor 7 in correspondence with said first portion of skin area and/or said third portion of said skin area, adjacent to said first portion of said skin area, when said image was acquired) or to the average of temperature values, if there is a plurality of sensors 7, combined with said image;

impedance value combined with said image (i.e., measured by sensor 15 in correspondence with said first portion of said skin area when said image has been acquired);

saturation value combined with said image (i.e., measured by sensor 20 in correspondence with said portion of said skin area when said image has been acquired).

In other words, the microprocessor 21 is suitable for combining values assumed by said first parameters and associated with an image acquired by the microscope 4 to:

the pH value combined with said image or with the average of pH values, if a plurality of sensors 6 is present, combined with said image;

the temperature value combined with said image or with the average of temperature values, if a plurality of sensors 7 is present, combined with said image;

the impedance value associated with said image;

the saturation value associated with said image.

If the microprocessor 21 includes the algorithms 30, when the device 1 is connected to the aforementioned apparatus by means of the port 29 or the antenna 27, the microprocessor 21 is also suitable for transmitting to the aforesaid apparatus one or more values assumed by said first parameters, calculated by the algorithms 30 and stored in the memory 31.

The algorithms 30 may comprise an expert system and/or a numerical classifier with a training system supervising the same.

The first parameters can be organized in a "feature vector" and consist, by way of example, in estimates of empirical characteristics such as roughness, pigmentation and hydration.

In light of the foregoing, if the microprocessor 21 includes the algorithms 30, the aforementioned smartphone, instead of or in addition to being able to receive from the device 1 the images acquired by the microscope 4, can receive from the device 1, in addition to the pH values, of temperature, impedance and saturation, the values assumed by said first parameters. From said smartphone, the values assumed by said first parameters, together with the pH, temperature, impedance and saturation values and possibly also the images acquired by the microscope 4, are easily forwarded to another person, such as a specialist, (such as a doctor or cosmetologist).

The algorithms 30, instead of being included in the device 1, could be included in the aforementioned device, that is, by way of example, in the aforementioned "app" of the smartphone. In this case, the smartphone can receive from the device 1 the images acquired by the microscope 4 and the values of pH, temperature, impedance and saturation respectively associated with them, and calculate, by means of the algorithms 30, the values assumed by said first ones parameters and associated with said images. From said smartphone, in addition or as an alternative to the images acquired by the microscope 4, the values assumed by said first parameters, together with the pH, temperature, impedance and saturation values respectively associated with them, are easily forwarded to another person, such as a specialist, (such as a doctor or cosmetologist).

In addition to the algorithms 30, the microprocessor 21 could comprise second algorithms 32 for the determination of values respectively assumed by second characteristic parameters of said first portion of said skin zone at least in correspondence with which the microscope 4 is suitable for acquiring images of said skin when the device 1 is in contact with the skin of a person in correspondence with said zone.

The microprocessor 21, by means of the algorithms 32, is in this case suitable for:

receive as input data:

the values assumed by said first parameters, stored in the memory 31 and calculated by the microprocessor 21 through the algorithms 30, receiving in input an image acquired by the microscope 4 in correspondence with at least said first portion of said area of the skin of a person (with said first portion of said skin area corresponding to the visual field of the microscope 4), when the device 1 is in contact with said skin in correspondence with said area and the pH value associated with them (i.e., measured by the sensor 6 in correspondence with said second portion of said skin area, adjacent to said first portion of said skin area, when said image has been acquired)

the average of pH values, if a plurality of sensors 6 is present, combined with them;

the temperature value associated with them (i.e., measured by the sensor 7 in correspondence with said first portion of the skin area and/or said third portion of said skin area, adjacent to said first portion of said skin area, when said image was acquired)

the average of temperature values, if there is a plurality of sensors 7, combined with them;

the impedance value associated with them (i.e., measured by the sensor 15 in correspondence with said first portion of said skin area when said image has been acquired);

the saturation value associated with them (i.e., measured by the sensor 20 in correspondence with said first portion of said skin area when said image has been acquired)

and for:

calculating values assumed by said second parameters and associated with said image (to which said values assumed by said first parameters and received at the input are in turn associated).

If the microprocessor 21 includes, in addition to the algorithms 30, also the algorithms 32, the device 1 comprises a seventh memory 33 suitable for containing the values assumed by said second parameters and calculated by the microprocessor 21 through the algorithms 32. The microprocessor 21 is also suitable to memorize in the memory 33 the values assumed by said second parameters and calculated by means of the algorithms 32. When the device is connected to the aforementioned apparatus by means of the port 29 or the antenna 27, the microprocessor 21 is suitable for transmitting a or more values assumed by said second parameters.

Like the algorithms 30, the algorithms 32 can comprise an expert system and/or a numerical classifier with a training system supervising the same.

The second parameters consist, by way of example, in so-called "fuzzy" estimates of the level of agreement of the first parameters with what is expected for specific pathological conditions.

In light of the foregoing, if the microprocessor 21 includes the algorithms 30 and 32, the aforementioned smartphone, instead of or in addition to being able to receive from the device 1 the images acquired by the microscope 4, the pH, temperature, impedance and respectively associated with them and/or the values assumed by said first parameters and respectively associated with them, it can receive from the device 1 the values assumed by said second parameters. From said smartphone, the values assumed by said second parameters are easily forwarded to another person, such as for example a specialist (such as a doctor or a cosmetologist).

The algorithms 32, instead of being included in the device 1, could be included in the aforementioned device, that is, by way of example, in the aforementioned "app" of the smartphone. In this case, the smartphone can receive from the device 1, the values assumed by said first parameters, possibly together with the images to which they are associated, and the pH, temperature, impedance and saturation values respectively associated with them, and calculate, by means of the algorithms 32, the values assumed by said second parameters are respectively associated with the same images to which the values assumed by said first parameters are associated. From said smartphone, in addition or as an alternative to the images acquired by the microscope 4, the values of pH, temperature, impedance and saturation respectively associated with them and the values assumed by said first parameters and respectively associated with them, the assumed values from said second parameters they can be easily forwarded to another person, such as for example a specialist, such as a doctor or a cosmetologist.

Another object of the invention is a system for conducting a multiparametric examination of the skin of a person. This system includes:

one or more devices 1;
    for each of the devices 1, the aforementioned device, such as for example a "smartphone", which can be connected to said device 1 for transmitting data between said device and the microprocessor 21 of said device 1, via port 29 or the antenna 27 of the latter;
    a server.

Each of said apparatus is suitable for establishing a connection with the server for the transmission of data between said apparatus and the server.

Each of these devices, when connected to the server, is also suitable for transmitting to the latter (i.e., the server):

one or more images acquired by the microscope 4 of the device 1 connectable to said apparatus and received by said apparatus by said device 1 when connected (said device 1) to said apparatus;
    one or more pH values measured by the sensor 6 of the device 1 connectable to said apparatus and received by said apparatus by said device 1 when connected (said device 1) to said apparatus;
    one or more temperature values measured by the sensor 7 of the device 1 connectable to said device and received by said device by said device 1 when connected (said device 1) to said device;
    one or more impedance values measured by the sensor 15 of the device 1 connectable to said device and received by said device by said device 1 when connected (said device 1) to said device;
    one or more saturation values measured by the sensor 20 of the device 1 connectable to said device and received from said device by said device 1 when connected (said device 1) to said device
    and/or
    if the microprocessor 21 of the devices 1 comprises the algorithms 30, one or more values assumed by said first parameters, calculated by the microprocessor 21, through the algorithms 30, of the device 1 connectable to said device and received from said device by said device 1 when connected (said device 1) to said device
    and/or
    if the microprocessor 21 of the devices 1 comprises the algorithms 32, one or more values assumed by said second parameters, calculated by the microprocessor 21, by means of the algorithms 32, of the device 1 connectable to said device and received from said device by said device 1 when connected (said device 1) to said device.

For each of these devices, the server is suitable for storing:

one or more images received from the server by said apparatus when connected (said apparatus) to the server;
    one or more pH values received from the server by said appliance when connected (said appliance) to the server;
    one or more temperature values received from the server by said appliance when connected (said appliance) to the server;
    one or more impedance values received from the server by said apparatus when connected (said apparatus) to the server;
    one or more saturation values received from the server by said appliance when connected (said appliance) to the server,
    and/or
    if the microprocessor 21 of the devices 1 comprises the algorithms 30, one or more values assumed by said first parameters and received by the server by said device when connected (said device) to the server
    and/or
    if the microprocessor 21 of the devices 1 comprises the algorithms 32, one or more values assumed by said second parameters and received from the server by said device when connected (said device) to the server.

The server advantageously allows you to store data acquired from multiple devices 1, for example in order to allow a doctor or a cosmetologist to access them, so as to be able to carry out a remote analysis of the skin conditions and possibly check the progress of therapies or treatments performed.

The algorithms 30 and 32, instead of being included in each device 1 or in each of said apparatuses, could be included in the aforementioned server.

On the basis of the description provided for a preferred embodiment example, it is obvious that some changes can be introduced by the person skilled in the art without thereby departing from the scope of the invention as defined by the following claims.

The invention claimed is:

1. A device for conducting a multi-parameter examination of a person's skin, said device comprising:

a housing at which said device:
        is configured to be grasped by the person and
        when grasped by the person, the device is configured to be brought into contact with said person's skin at a zone of said skin to perform the multi-parameter examination in said zone;
    a skin microscope included in said device so that, when said device is in contact with the person's skin at said skin zone, said microscope is configured to acquire an image of at least a first portion of said skin zone;
    a plurality of illuminators configured to emit electromagnetic radiation in at least one range of wavelengths, each of said illuminators configured to emit electromagnetic radiation having a wavelength not less than 100 nm and not above 1 mm;
    at least one illuminator of the plurality of illuminators configured to emit electromagnetic radiation and included in said device so that, when said device is in contact with the person's skin at said skin zone, the electromagnetic radiation emitted by said illuminator impinges on said skin zone at least at said first portion of said skin zone and, once at least partially reflected and/or scattered by said first portion of said skin zone, impinges, at least partially, on optics of said microscope;

first measuring means configured to measure pH and included in said device so that, when said device is in contact with the person's skin at said skin zone, said first measuring means are configured to measure the pH of said person's skin at least at a second portion of said skin zone adjacent to said first portion of said skin zone;

second measuring means configured to measure temperature and included in said device so that, when said device is in contact with the person's skin at said skin zone, said second measuring means are configured to measure the temperature of said person's skin at least at said first portion of said skin zone and/or at least at a third portion of said skin zone adjacent to said first portion of said skin zone;

third measuring means configured to measure impedance of the person's body tissues, said third measuring means comprising at least one pair of electrodes included in said device so that, when said device is in contact with the person's skin at said skin zone, said electrodes are in contact with said person's skin on opposite sides with respect to said first portion of said skin zone, respectively, wherein said third measuring means are configured to apply a potential difference between said pair of electrodes, when said device is in contact with the person's skin at said skin zone, wherein said third measuring means is further configured to calculate the impedance of body tissues included in said zone, at least at said first portion of said skin zone, by measuring an alternating electric current crossing said body tissues upon the application of a potential difference thereto by means of said electrodes;

fourth measuring means configured to measure the hemoglobin oxygen saturation in the person's peripheral blood, said fourth measuring means comprising at least one emitter configured to emit electromagnetic radiation having a wavelength between 600 nm and 1000 nm and at least one receiver configured to receive electromagnetic radiation having a wavelength between 600 nm and 1000 nm, said emitter and said receiver included in said device so that, when said device is in contact with the person's skin at said skin zone, the electromagnetic radiation emitted by said emitter impinges on said zone at least at said first portion of said skin zone and, once at least partially reflected and/or scattered by said first portion of said skin zone, impinges, at least partially, on said receiver, wherein when said device is in contact with the person's skin at said skin zone, said fourth measuring means being configured to calculate the hemoglobin oxygen saturation present in the peripheral blood in said skin zone, at least at said first portion of said skin zone, by measuring the wavelength of electromagnetic radiation impinging on said receiver once emitted by said emitter and reflected and/or scattered by said first portion of said skin zone;

a first memory configured to contain images acquired by said microscope;

a second memory configured to contain pH values measured by said first measuring means;

a third memory configured to contain temperature values measured by said second measuring means;

a fourth memory configured to contain impedance values measured by said third measuring means;

a fifth memory configured to contain saturation values measured by said fourth measuring means;

control means for said microscope, said illuminators and said first, second, third and fourth measuring means, said control means being configured to store:

images acquired by said microscope in said first memory;

pH values measured by said first measuring means in said second memory;

temperature values measured by said second measuring means in said third memory;

impedance values measured by said third measuring means in said fourth memory; and oxygen saturation values measured by said fourth measuring means in said fifth memory, said control means being further configured to combine images acquired by said microscope at least at said first portion of said skin zone, when said device is in contact with the person's skin at said skin zone, with respectively:

pH values measured by said first measuring means at said second portion of said skin zone when said images were acquired, respectively;

temperature values measured by said second measuring means at said first portion of said skin zone and/or said third portion of said skin zone when said images were acquired, respectively;

impedance values measured by said third measuring means at said first portion of said skin zone when said images were acquired, respectively; and oxygen saturation values measured by said fourth measuring means at said first portion of said skin zone when said images were acquired, respectively; and connecting means adapted to establish a connection between said device and an electronic apparatus for transceiving data between said control means and said apparatus, when said device is connected to said apparatus through said connecting means, said control means configured to transmit to said apparatus:

one or more images acquired by said microscope;

one or more pH values measured by said first measuring means;

one or more temperature values measured by said second measuring means;

one or more impedance values measured by said third measuring means; and one or more oxygen saturation values measured by said four measuring means, when said device is connected to said apparatus through said connecting means, said control means being further configured to receive activation commands of said microscope, said illuminators and said first, second, third and fourth measuring means from said apparatus.

2. The device according to claim 1, wherein at least five of said illuminators configured to emit electromagnetic radiation included in the following five ranges, respectively: between 315 nm and 400 nm, between 315 nm and 740 nm, between 500 nm and 650 nm, between 625 nm and 740 nm, and between 700 nm and 800 nm.

3. The device according to claim 2, wherein said first measuring means are included in said device so that, when said device is in contact with the person's skin at said skin zone, said first measuring means are configured to measure the pH of said person's skin at least at a point of an edge delimiting said first portion of said skin zone, said edge being at least partially in common with said second portion of said skin zone.

4. The device according to claim 2, wherein said second measuring means are included in said device so that, when said device is in contact with the person's skin at said skin zone, said second measuring means are configured to measure the are suitable for measuring temperature of said person's skin at least at a point of an edge delimiting said first portion of said skin zone, said edge, at a point of which said second measuring means are configured to measure the temperature of said person's skin, being at least partially in common with said third portion of said skin zone.

5. The device according to claim 2, wherein said second measuring means comprise an infrared electromagnetic radiation thermometer, said thermometer being included in said device so that, when said device is in contact with the person's skin at said skin zone, said thermometer is configured to receive infrared electromagnetic radiation radiated by said first portion of said skin zone, so as to be configured to measure the temperature of said person's skin at said first portion of said skin zone.

6. The device according to claim 1, wherein said first measuring means are included in said device so that, when said device is in contact with the person's skin at said skin zone, said first measuring means are configured to measure the pH of said person's skin at least at a point of an edge delimiting said first portion of said skin zone, said edge being at least partially in common with said second portion of said skin zone.

7. The device according to claim 6, wherein said first measuring means are included in said device so that, when said device is in contact with the person's skin at said skin zone, said first measuring means are configured to measure the pH of said person's skin in a plurality of points of said edge, said first measuring means being further configured to average the pH values measured in said plurality of points of said edge, respectively, to estimate the pH of said person's skin at said first portion of said skin zone, said average of pH values being storable in said second memory, combinable with an image acquired by said microscope, and transmissible to said apparatus instead of a pH value measured by said first measuring means.

8. The device according to claim 1, wherein said second measuring means are included in said device so that, when said device is in contact with the person's skin at said skin zone, said second measuring means are configured to measure the temperature of said person's skin at least at a point of an edge delimiting said first portion of said skin zone, said edge, at a point of which said second measuring means are configured to measure the temperature of said person's skin, being at least partially in common with said third portion of said skin zone.

9. The device according to claim 6, wherein said second measuring means are included in said device so that, when said device is in contact with the person's skin at said skin zone, said second measuring means are configured to measure the temperature of said person's skin at least at a point of an edge delimiting said first portion of said skin zone, said edge, at a point of which said second measuring means are configured to measure the temperature of said person's skin, being at least partially in common with said third portion of said skin zone.

10. The device according to claim 6, wherein said second measuring means comprise an infrared electromagnetic radiation thermometer, said thermometer being included in said device so that, when said device is in contact with the person's skin at said skin zone, said thermometer is configured to receive infrared electromagnetic radiation radiated by said first portion of said skin zone, so as to be configured to measure the temperature of said person's skin at said first portion of said skin zone.

11. The device according to claim 7, wherein said second measuring means are included in said device so that, when said device is in contact with the person's skin at said skin zone, said second measuring means are configured to measure the temperature of said person's skin at least at a point of an edge delimiting said first portion of said skin zone, said edge, at a point of which said second measuring means are configured to measure the temperature of said person's skin, being at least partially in common with said third portion of said skin zone.

12. The device according to claim 7, wherein said second measuring means comprise an infrared electromagnetic radiation thermometer, said thermometer being included in said device so that, when said device is in contact with the person's skin at said skin zone, said thermometer is configured to receive infrared electromagnetic radiation radiated by said first portion of said skin zone, so as to be configured to measure the temperature of said person's skin at said first portion of said skin zone.

13. The device according to claim 8, wherein said second measuring means are included in said device so that, when said device is in contact with the person's skin at said skin zone, said second measuring means are configured to measure the temperature of said person's skin in a plurality of points of said edge at least partially in common with said third portion of said skin zone, said second measuring means being further configured to average the temperature values measured in said plurality of points of said edge at least partially in common with said third portion of said skin zone, respectively, so as to estimate the temperature of said person's skin at said first portion of said skin zone, said average of temperature values being storable in said third memory, combinable with an image acquired by said microscope, and transmissible to said apparatus instead of a temperature value measured by said second measuring means.

14. The device according to claim 1, wherein said second measuring means comprise an infrared electromagnetic radiation thermometer, said thermometer being included in said device so that, when said device is in contact with the person's skin at said skin zone, said thermometer is configured to receive infrared electromagnetic radiation radiated by said first portion of said skin zone, so as to be configured to measure the temperature of said person's skin at said first portion of said skin zone.

15. The device according to claim 1, wherein said third measuring means, when said device is in contact with the person's skin at said skin zone, are configured to apply, by means of said pair of electrodes, to body tissues included in said skin zone at least at said first portion of said skin zone, potential differences such that said alternating electric current crossing said body tissues, upon the application of said potential differences to said body tissues, crosses said body tissues in two or more frequency ranges, each between 1 kHz and 1 MHz.

16. The device according to claim 1, wherein said emitter of said fourth measuring means and said receiver of said fourth measuring means lie on opposite sides with respect to the optics of said microscope, said emitter being oriented so that, when said emitter emits electromagnetic radiation, said electromagnetic radiation are emitted away from the optics of said microscope.

17. The device according to claim 1, wherein said receiver of said fourth measuring means is housed inside the optics of said microscope.

18. The device according to claim 1, wherein said control means comprise first algorithms for determining values taken by first characteristic parameters of images acquired by said microscope, respectively, said control means, through said first algorithms, being suitable for configured to:

receive as input data one of said images acquired by said microscope and calculate values taken by said first parameters and associated with said input image received, said device comprising a sixth memory configured to contain values taken by said first parameters and calculated by said control means through said first algorithms, said control means being configured to store in said sixth memory values taken by said first parameters and calculated through said first algorithms, said control means being configured to combine values taken by said first parameters and associated with one of said images acquired by said microscope, with:

said pH value combined with said image or said average of pH values, if obtainable by said first measuring means, combined with said image;

said temperature value combined with said image or said average of temperature values, if obtainable by said second measuring means, combined with said image;

said impedance value combined with said image; and said oxygen saturation value combined with said image, when said device is connected to said apparatus through said connecting means, said control means being configured to transmit to said apparatus one or more values taken by said first parameters and calculated through said algorithms.

19. The device according to claim 18, wherein said control means comprise second algorithms for determining values taken, respectively, by second characteristic parameters of said first portion of said skin zone at least at which said microscope is suitable for acquiring configured to acquire images of said skin when said device is in contact with said skin at said zone, said control means, through said second algorithms, being configured to:

receive as input data:

values taken by said first parameters and calculated by said control means through said first algorithms receiving as input one of said images acquired by said microscope at least at said first portion of said skin zone, when said device is in contact with said skin at said zone and said pH value combined therewith or said average of pH values, if obtainable by said first measuring means, combined therewith;

the temperature value combined therewith or said average of temperature values, if obtainable by said second measuring means, combined therewith;

said impedance value combined therewith; and said oxygen saturation value associated therewith and for:

calculating values taken by said second parameters and associated with said image, said device comprising a seventh memory configured to contain values taken by said second parameters and calculated by said control through said second algorithms, said control means being configured to store in said seventh memory values taken by said second parameters and calculated through said second algorithms, when said device is connected to said apparatus through said connecting means, said control means being configured to transmit to said apparatus one or more values taken by said second parameters and calculated through said second algorithms.

20. A system for conducting a multi-parameter examination of a person's skin, said system comprising:

one or more devices according to claim 1;

for each of said devices, said electronic apparatus being connectable to said device for transceiving data between said apparatus and said control means of said device, through said connecting means of said device;

a server, each of said apparatuses being configured to establish a connection with said server for transceiving data between said apparatus and said server, each of said apparatuses, when connected to said server, being further configured to transmit to the server:

one or more images acquired by said microscope of said device, being connectable to said apparatus, and received from said apparatus by said device when connected to said apparatus;

one or more pH values measured by said first measuring means of said device or one or more said averages of pH values if obtainable by said first measuring means of said device, being connectable to said apparatus, and received from said apparatus by said device when connected said apparatus;

one or more temperature values measured by said second measuring means of said device or one or more said averages of temperature values if obtainable by said second measuring means of said device, being connectable to said apparatus, and received from said apparatus by said device when connected to said apparatus;

one or more impedance values measured by said third measuring means of said device, being connectable to said apparatus, and received from said apparatus by said device when connected to said apparatus; and one or more oxygen saturation values measured by said fourth measuring device of said device, being connectable to said apparatus, and received from said apparatus by said device when connected to said apparatus and/or if said control means of said devices comprise said first algorithms, one or more values taken by said first parameters and calculated by said control means, through said first algorithms, of said device being connectable to said apparatus, and received from said apparatus by said device when connected to said apparatus and/or if said control means of said devices comprise said second algorithms, one or more values taken by said second parameters and calculated by said control means, through said second algorithms, of said device being connectable to said apparatus, and received from said apparatus by said device when connected to said apparatus, for each of said apparatuses, said server being configured to store:

said one or more images received from said server by said apparatus when connected to said server;

said one or more pH values, or said one or more averages of pH values, received from said server by said apparatus when connected to said server;

said one or more temperature values, or said one or more averages of temperature values, received from said server by said apparatus to said server;

said one or more impedance values received from said server by said apparatus when connected to said server; and said one or more oxygen saturation values received from said server by said apparatus when connected to said server, and/or if said control means of said devices comprise said first algorithms, said one or more values taken by said first parameters and received from said server by said apparatus when connected to said server and/or if said control means of said devices comprise said second algorithms, said one or more values taken by said second parameters and received from said server by said apparatus when connected to said server.

\* \* \* \* \*